(12) United States Patent
Okada et al.

(10) Patent No.: US 6,174,900 B1
(45) Date of Patent: *Jan. 16, 2001

(54) SUBSTITUTED PIPERIDINE DERIVATIVE FOR TREATING URINARY DISTURBANCE

(75) Inventors: Tomomi Okada, Narita; Fujiko Konno, Tomisato-machi; Terumitsu Kaihoh, Narita; Masago Ishikawa, Shisui-machi; Yoshinori Takahashi, Tomisato-machi; Hiroyuki Mizuno, Tomisato-machi; Haruyoshi Honda, Tomisato-machi; Susumu Sato, Narita; Hideaki Matsuda, Abiko, all of (JP)

(73) Assignee: SS Pharmaceutical Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/332,444

(22) Filed: Jun. 14, 1999

Related U.S. Application Data

(63) Continuation of application No. 08/672,058, filed on Jun. 26, 1996, now Pat. No. 5,968,956.

(30) Foreign Application Priority Data

Jun. 26, 1995 (JP) .................................... 7-159329

(51) Int. Cl.$^7$ ........................ A61K 31/445; C07D 211/46
(52) U.S. Cl. ........................ 514/317; 514/256; 514/318; 514/326; 514/329; 544/233; 544/242; 544/336; 546/194; 546/208; 546/209; 546/210; 546/213; 546/224
(58) Field of Search .................. 514/318, 317, 514/326, 329, 252, 256; 546/194, 208, 209, 210, 213, 224; 544/242, 336

(56) References Cited

U.S. PATENT DOCUMENTS 5,236,956 * 8/1993 Sjogren ................. 514/617

5,750,540 5/1998 Tsuchiya et al. ................. 514/318

FOREIGN PATENT DOCUMENTS

| 0 581 167 A1 | 2/1994 | (EP) . |
| 863141 * | 9/1998 | (EP) . |
| 92/06958 * | 4/1992 | (WO) . |
| WO 93/16048 | 8/1993 | (WO) . |

OTHER PUBLICATIONS

Patent Abstracts of Japan, vol. 018, No. 443 (C–1239), Aug. 18, 1994 & JP 06 135958 A (TAABE Seiyaku Co. Ltd.), May 17, 1994.

* cited by examiner

*Primary Examiner*—Ceila Chang
(74) *Attorney, Agent, or Firm*—Oblon, Spivak, McClelland, Maier & Neustadt, P.C.

(57) ABSTRACT

Disclosed herein is a substituted piperidine derivative represented by the following general formula (1):

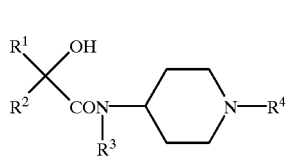

(I)

wherein $R^1$ means an aryl or heteroaryl group which may have at least one substituent, $R^2$ denotes an alkyl, alkenyl or aralkyl group, $R^3$ stands for a hydrogen atom or an alkyl group, and $R^4$ is a hydrogen atom, an alkyl group, or an aryl, heteroaryl, aralkyl, aralkenyl or heteroaralkyl group which may have at least one substituent, or a salt thereof. A medicine including this compound is also disclosed. The compound has excellent anticholinergic effect and calcium antagonism and inhibits reflex bladder contraction and is hence useful for prophylaxis of and treatment for a urinary disturbance such as pollakiuria.

6 Claims, No Drawings

SUBSTITUTED PIPERIDINE DERIVATIVE FOR TREATING URINARY DISTURBANCE

This application is a Continuation of U.S. application Ser. No. 08/672,058, filed on Jun. 26, 1996, now U.S. Pat. No. 5,968,956.

BACKGROUND OF THE INVENTION

1. Field of the Invention

The present invention relates to a novel substituted piperidine derivative and a salt thereof, and particularly to a substituted piperidine derivative and a salt thereof, which have an anticholinergic effect and a calcium antagonism and are useful as medicines for prophylaxis of and treatment for a urinary disturbance such as nervous pollakiuria, neurogenic bladder, nocturnal enuresis, unstable bladder, pollakiuria caused by a disease such as chronic cystitis, or urinary incontinence.

2. Description of the Background Art

In order to prevent and treat a urinary disturbance such as nervous pollakiuria, neurogenic bladder, nocturnal enuresis, unstable bladder, pollakiuria caused by a disease such as chronic cystitis, or urinary incontinence, drugs which inhibit reflex bladder contraction are useful.

As drugs for inhibiting the reflex bladder contraction, oxybutynin hydrochloride, propiverine hydrochloride, vamicamide and compounds described in Japanese Patent Application Laid-Open Nos. 92921/1994 and 135958/1994 and WO 93/16048 have heretofore been reported.

However, the conventional compounds have been found to be insufficient in the inhibitory effect on the reflex bladder contraction.

SUMMARY OF THE INVENTION

It is accordingly an object of the present invention to provide a compound which effectively inhibits reflex bladder contraction and is useful as a medicine for prophylaxis of and treatment for a urinary disturbance.

With the foregoing circumstances in view, the present inventors have carried out an extensive investigation. As a result, the inventors have synthesized a novel substituted piperidine derivative represented by the general formula (1), which will be described subsequently, and found that this compound has an anticholinergic effect and a calcium antagonism and effectively inhibits reflex bladder contraction and is hence useful as an agent for preventing and treating a urinary disturbance, thus leading to completion of the present invention.

According to the present invention, there is thus provided a substituted piperidine derivative represented by the following general formula (1):

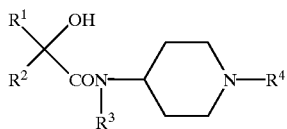

(I)

wherein $R^1$ means an aryl or heteroaryl group which may have at least one substituent, $R^2$ denotes an alkyl, alkenyl or aralkyl group, $R^3$ stands for a hydrogen atom or an alkyl group, and $R^4$ is a hydrogen atom, an alkyl group, or an aryl, heteroaryl, aralkyl, aralkenyl or heteroaralkyl group which may have at least one substituent, or a salt thereof.

According to the present invention, there is also provided a medicine comprising the substituted piperidine derivative or the salt thereof as an active ingredient.

According to the present invention, there is further provided a medicine composition comprising the substituted piperidine derivative or the salt thereof and a pharmaceutically permissible carrier.

According to the present invention, there is still further provided use of the substituted piperidine derivative or the salt thereof for a medicine.

According to the present invention, there is yet still further provided a method for treating a urinary disturbance, which comprises administering an effective amount of the substituted piperidine derivative or the salt thereof.

The substituted piperidine derivative (1) according to the present invention or the salt thereof has excellent anticholinergic effect and calcium antagonism and effectively inhibits reflex bladder contraction and is hence useful as an agent for preventing and treating a urinary disturbance such as nervous pollakiuria, neurogenic bladder, nocturnal enuresis, unstable bladder, pollakiuria caused by a disease such as chronic cystitis, or urinary incontinence.

The above and other objects, features and advantages of the present invention will be readily appreciated as the same becomes better understood from the preferred embodiments of the present invention, which will be described subsequently in detail, and from the appended claims.

DETAILED DESCRIPTION OF THE PREFERRED EMBODIMENTS

The substituted piperidine derivative according to the present invention is represented by the general formula (1). Examples of the aryl group indicated by $R^1$ in the formula (1) include phenyl and naphthyl groups, while examples of the heteroaryl group include thienyl, pyridyl, pyrimidyl and pyrazyl groups. Examples of radicals which may be substituted on the aryl or heteroaryl group indicated by $R^1$ include halogen atoms, and alkyl, halogenoalkyl, alkoxyl, amino, benzyloxy, cyano, benzoyl, alkanoyl, carbamoyl, carboxyl, alkanoyloxy, nitro and sulfonamide groups. Of these, preferred are one to three radicals selected from the group consisting of halogen atoms, halogenated $C_{1-6}$ alkyl groups, $C_{1-6}$ alkyl groups, $C_{1-6}$ alkoxyl groups, an amino group, a benzyloxy group, a cyano group, a benzoyl group, $C_{1-6}$ alkanoyl groups, a carbamoyl group, a carboxyl group, $C_{1-6}$ alkanoyloxy groups, a nitro group and a sulfonamide group. More preferred are one to three radicals selected from the group consisting of halogen atoms, halogenated $C_{1-6}$ alkyl groups, $C_{1-6}$ alkyl groups, $C_{1-6}$ alkoxyl groups and an amino group. Still more preferred are one to three radicals selected from the group consisting of halogen atoms, $C_{1-6}$ alkyl groups, halogenated $C_{1-6}$ alkyl groups and $C_{1-6}$ alkoxyl groups. Most preferred are one to three radicals selected from the group consisting of halogen atoms, and methyl, trifluoromethyl and methoxyl groups.

As $R^1$, the aryl or heteroaryl group which may have at least one of the above substituents are preferred, with the phenyl, thienyl or pyridyl group which may have at least one of the above substituents being particularly preferred.

Examples of the alkyl group indicated by $R^2$ include linear, branched, cyclic and cyclic-linear alkyl groups having 1–8 carbon atoms. The linear alkyl groups having 1–8 carbon atoms include methyl, ethyl n-propyl, n-butyl, n-pentyl, n-hexyl, n-heptyl and n-octyl groups. Examples of the branched alkyl groups include isopropyl, isobutyl, sec-butyl, 3-pentyl and 2-ethylhexyl groups. The cyclic alkyl groups include cyclopropyl, cyclobutyl, cyclopentyl, cyclohexyl, cycloheptyl and cyclooctyl groups. Examples of the cyclic-linear alkyl groups include cyclopropylmethyl and cyclohexylmethyl groups. Of these, the branched or cyclic alkyl groups are particularly preferred.

Examples of the alkenyl group indicated by $R^2$ include alkenyl groups having 2–6 carbon atoms. Specific examples thereof include vinyl and allyl groups, with the vinyl group being particularly preferred.

Examples of the aralkyl group indicated by $R^2$ include phenyl-$C_{1-6}$-alkyl and naphthyl-$C_{1-6}$-alkyl groups. Of these, the phenyl-$C_{1-6}$-alkyl groups are preferred, with a benzyl group being particularly preferred.

Examples of the alkyl group indicated by $R^3$ include alkyl groups having 1–6 carbon atoms. Specific examples thereof include methyl and ethyl groups, and linear or branched propyl, butyl, pentyl and hexyl groups. Of these, the methyl group is particularly preferred. As $R^3$, a hydrogen atom or a methyl group is particularly preferred.

As the alkyl group indicated by $R^4$, those having 1–6 carbon atoms are preferred. Examples thereof include methyl and ethyl groups, and linear or branched propyl, butyl, pentyl and hexyl groups. Examples of the aryl group include phenyl and naphthyl groups. Examples of the heteroaryl group include thienyl, pyridyl, pyrimidyl and pyrazyl groups. Examples of the aralkyl group include phenyl-$C_{1-6}$-alkyl groups. Specific examples thereof include benzyl, phenethyl and phenylpropyl groups. Examples of the heteroaralkyl group include heteroaryl-$C_{1-6}$-alkyl groups. Specific examples thereof include pyridylmethyl, pyrimidylmethyl, pyrazylmethyl, pyridylethyl, pyrimidylethyl and pyrazylethyl groups. Examples of the aralkenyl group include phenyl-$C_{2-6}$-alkenyl groups. Specific examples thereof include styryl and cinnamyl groups.

Examples of radicals which may be substituted on the aryl, heteroaryl, aralkyl, aralkenyl or heteroaralkyl group indicated by $R^4$ include one to three radicals selected from the group consisting of $C_{1-6}$ alkoxyl groups, halogen atoms, a cyano group, a hydroxyl group, a nitro group, an amino group, $C_{1-6}$ alkylamino groups and $C_{1-6}$ alkoxycarbonyl groups. Examples of the $C_{1-6}$ alkoxyl groups include methoxyl, ethoxyl and isopropoxyl groups, with the methoxyl group being particularly preferred. Examples of the $C_{1-6}$ alkoxycarbonyl groups include methoxycarbonyl and ethoxycarbonyl groups, with the methoxycarbonyl group being particularly preferred.

As $R^4$, a hydrogen atom, or a $C_{1-6}$ alkyl, phenyl, phenyl-$C_{1-6}$-alkyl, phenyl-$C_{2-6}$-alkenyl or pyridyl-$C_{1-6}$-alkyl group (wherein the phenylalkyl, phenylalkenyl or pyridylalkyl group may be substituted by one to three substituents selected from the group consisting of $C_{1-6}$ alkoxyl groups, halogen atoms, a cyano group, a hydroxyl group, a nitro group, an amino group, $C_{1-6}$ alkylamino groups and $C_{1-6}$ alkoxycarbonyl groups) is particularly preferred.

No particular limitation is imposed on the salt of the substituted piperidine derivative (1) according to the present invention so far as it is a pharmaceutically permissible salt. Examples thereof include organic acid salts such as the formate, acetate, trifluoroacetate, fumarate, maleate, succinate, methanesulfonate and p-toluenesulfonate; inorganic acid salts such as the hydrochloride, hydrobromate, hydriodate, sulfate and phosphate. Since the substituted piperidine derivative (1) has an asymmetric carbon atom, stereoisomers exist. All these isomers are included in the present invention. Further, the substituted piperidine derivative (1) may be present in the form of solvates typified by hydrates.

The substituted piperidine derivative (1) according to the present invention can be prepared in accordance with, for example, the following preparation processes 1–5.

Preparation process 1:

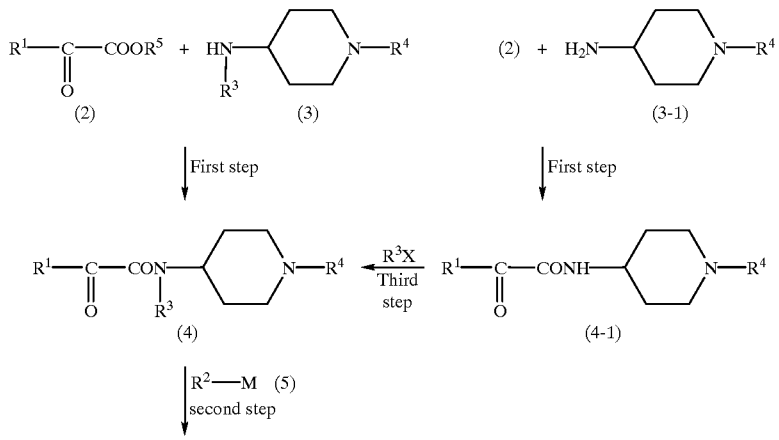

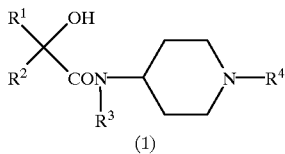

wherein $R^1$ to $R^4$ have the same meaning as defined above, $R^5$ denotes a lower alkyl group, and M is an alkali metal or MgX in which X is a halogen atom.

According to the preparation process 1, a compound (3) or a compound (3-1) is condensed with an α-ketoester (2) (the first step), and a compound (5) is subsequently reacted with the condensate (4) formed (the second step), thereby obtaining a compound (1) according to the present invention. The compound (4) may also be obtained by reacting a compound (4-1) with $R^3X$ (the third step).

The α-ketoester (2) used in the first step can be prepared in accordance with, for example, the method described in J.O.C., 46, 213 (1981); or Synthetic Communication, 11, 943 (1981). On the other hand, the compound (3) can be prepared in accordance with, for example, the method described in Organic Reactions, 4, 174 (1948).

The reaction in the first step is performed in the presence of a solvent or without any solvent. No particular limitation is imposed on the solvent used so far as it does not affect the reaction. Examples of the solvent include hydrocarbons such as benzene, toluene and xylene; ethers such as tetrahydrofuran and dioxane; amides such as dimethylformamide, dimethylacetamide and N-methyl-α-pyrrolidone; alcohols such as ethanol, butanol, methoxyethanol and ethoxyethanol; and sulfoxides such as dimethylsulfoxide. The reaction is carried out at a temperature ranging from room temperature to a reflux temperature. The reaction time is within a range of 0.5–8 hours. Most preferably, the reaction is conducted for 1–3 hours at 100–120° C. on an oil bath by using the compound (3) in a proportion of 2 moles per mole of the compound (2) without any solvent.

The compound (5) used in the second step can be prepared from $R^2$-X (X has the same meaning as defined above) in accordance with a method known per se in the art. The reaction in the second step is generally carried out in the presence of a solvent. No particular limitation is imposed on the solvent used so far as it does not affect the reaction. Examples of the solvent include diethyl ether, tetrahydrofuran and n-hexane.

The reaction in the third step is generally carried out in the presence of a suitable base and a solvent. Examples of the base used include sodium hydride, potassium t-butoxide, sodium hydroxide and potassium hydroxide. No particular limitation is imposed on the solvent used so far as it does not affect the reaction. Examples of the solvent include ethers such as ethyl ether, tetrahydrofuran and dioxane; mixed solvents such as dioxane-water; alcohols such as methanol and ethanol; amides such as dimethylformamide, dimethylacetamide and N-methyl-α-pyrrolidone; and sulfoxides such as dimethylsulfoxide. Besides, no particular limitation is imposed on the reaction temperature, and it is only necessary to conduct the reaction at a temperature ranging from room temperature to a reflux temperature.

Preparation process 2:

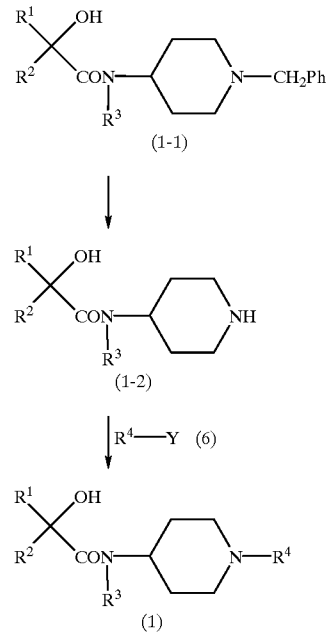

wherein $R^1$ to $R^4$ have the same meaning as defined above, and Y denotes a halogen atom or a sulfonyloxy group.

According to the preparation process 2, a compound (1-1) is catalytically hydrogenated to obtain a compound (1-2), and a compound (6) is reacted with the thus-obtained compound, thereby obtaining a compound (1) according to the present invention.

Suitable examples of a catalyst used in the catalytic hydrogenation include palladium catalysts such as palladium-carbon, palladium black and palladium hydroxide; platinum catalysts such as platinum oxide and platinum black; and nickel catalysts such as Raney nickel. The reaction is generally carried out in the presence of a solvent. No particular limitation is imposed on the solvent so far as it does not affect the reaction. Examples of the solvent used include methanol, ethanol, dioxane and dimethylformamide. Besides, no particular limitation is imposed on the reaction temperature, and in general, it is only necessary to conduct the reaction at room temperature or under heat.

Suitable examples of the radical Y in the compound (6) include fluorine, chlorine bromine and iodine atoms, and mesyloxy and tosyloxy groups.

The reaction of the compound (1-2) with the compound (6) is generally performed in the presence of a suitable base and a solvent. Examples of the base used include inorganic bases such as sodium hydroxide, potassium hydroxide, sodium carbonate and potassium carbonate, and organic bases such as triethylamine and pyridine. No particular limitation is imposed on the solvent used so far as it does not affect the reaction. Examples of the solvent include ethers such as ethyl ether, tetrahydrofuran and dioxane; mixed solvents such as dioxane-water; chlorinated hydrocarbons such as dichloromethane and chloroform; alcohols such as methanol and ethanol; and amides such as dimethylformamide, dimethylacetamide and N-methyl-α-pyrrolidone. Besides, no particular limitation is imposed on the reaction temperature, and it is only necessary to conduct the reaction at a temperature ranging from room temperature to a reflux temperature under heat.

Preparation process 3:

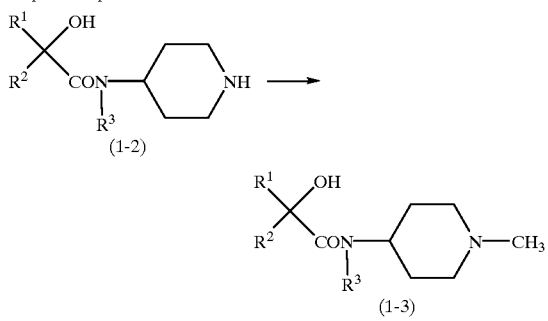

wherein $R^1$ to $R^3$ have the same meaning as defined above.

According to the preparation process 3, the compound (1-2) is subjected to reductive methylation, thereby obtaining a compound (1-3) according to the present invention.

Specifically, the reductive methylation is conducted by reacting formalin and formic acid with the compound (1-2). The reaction is performed in the presence of a solvent or without any solvent. No particular limitation is imposed on the solvent used so far as it does not affect the reaction. Examples thereof include acetonitrile and tetrahydrofuran. The reaction is conducted at a temperature ranging from room temperature to a reflux temperature under heat. Suitable reaction time is within a range of 1–3 hours.

Preparation process 4:

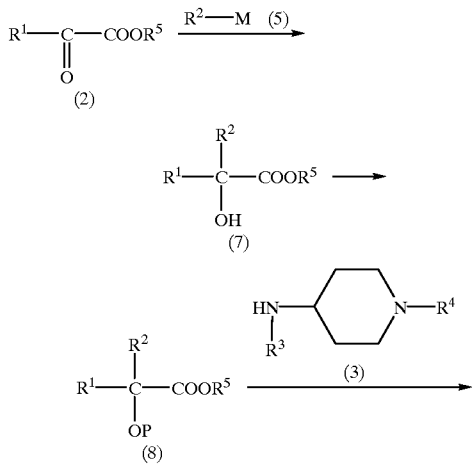

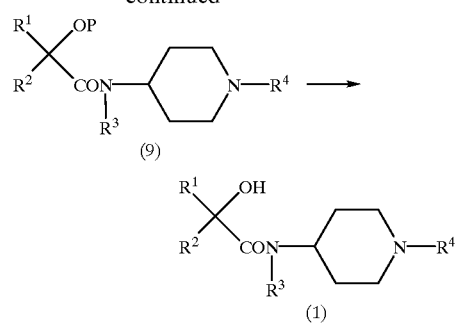

wherein $R^1$ to $R^5$ and M have the same meaning as defined above, and P denotes a protecting group for the hydroxyl group.

According to the preparation process 4, the compound (5) is reacted with the α-ketoester (2) to form an α-hydroxyester (7). After the hydroxyl group of the hydroxyester (7) is protected, the compound (3) is reacted with a compound (8) formed, and the protecting group for the hydroxyl group is then removed, thereby obtaining a compound (1) according to the present invention.

The reaction of the α-ketoester with the compound (5) is conducted in the same manner as in the second step in the preparation process 1. As a means for protecting the hydroxyl group of the compound (7), may be mentioned, for example, the means described in T. W. Green, Protective Groups in Organic Synthesis. The reaction of the formed compound (8) with the compound (3) is conducted in the same manner as in the first step in the preparation process 1. The removal of the protecting group for the hydroxyl group from the resulting compound (9) can be performed in accordance with, for example, the method described in T. W. Green, Protective Groups in Organic Synthesis.

Preparation process 5:

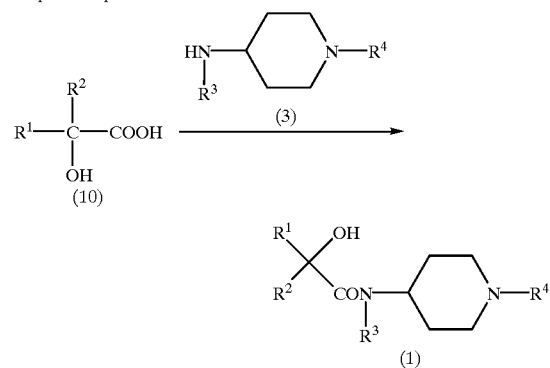

According to the preparation process 5, an α-hydroxycarboxylic acid (10) is reacted with the compound (3) in the presence of a suitable condensing agent, thereby obtaining a compound (1) according to the present invention.

The compound (10) can be prepared by hydrolyzing the compound (7) obtained in, for example, the preparation process (4) in accordance with a method known per se in the art.

Examples of the suitable condensing agent used in the preparation process 5 include carbonyldiimidazole, 1-hydroxy-2(1H)-pyridone, 1-hydroxy-1H-benzotriazole, N-hydroxysuccinimide, diphenylphosphorylazide, N,N-dicyclohexylcarbodiimide and 1-ethyl-3-(3-dimethylaminopropyl)-carbodiimide hydrochloride. The reaction is carried out in the presence of a suitable base, for example, an organic base such as triethylamine or pyridine according to the kind of the condensing agent. No particular limitation is imposed on a solvent used so far as it does not affect the reaction. Examples thereof include diethyl ether, tetrahydrofuran, chloroform, dichloromethane and N,N-dimethylformamide.

The isolation and purification of the intended compound in each of the above reactions can be conducted in accordance with a method known per se in the art, for example, washing, extraction, recrystallization, chromatography and/or the like. The conversion of such a compound to a salt may also be conducted in a method known per se in the art.

The compound (1) according to the present invention has excellent anticholinergic effect and calcium antagonism and inhibits reflex bladder contraction and is hence useful as a medicine for preventing and treating a urinary disturbance such as nervous pollakiuria, neurogenic bladder, nocturnal enuresis, unstable bladder, pollakiuria caused by a disease such as chronic cystitis, or urinary incontinence.

When the compound according to the present invention is used as such a medicine, it is only necessary to mix the compound with a solid or liquid carrier known in the technical fields concerned so as to prepare a medicine composition (a medicinal preparation) suitable for parenteral administration, oral administration or external administration. Examples of the medicinal preparation include liquid preparations such as, for example, injections, inhalants, syrups and emulsions, solid preparations such as, for example, tablets, capsules and granules, and external preparations such as, for example, ointments and suppositories. These preparations may contain additives routinely used, such as auxiliaries, stabilizers, wetting agents, emulsifiers, absorbefacients and surfactants, as needed. Examples of the additives include water for injection, Ringer's injection, glucose, sucrose syrup, gelatin, edible oil, cacao butter, magnesium stearate and talc.

When the compound according to the present invention is used as an agent for preventing and treating a urinary disturbance, its dose varies according to an administration method, and the age, weight, diseased condition of a patient to be dosed. However, it is preferably dosed in a proportion of 0.1–1,000 mg per day for an adult in the case of oral administration.

The present invention will hereinafter be described more specifically by the following examples. However, it goes without saying that the present invention is not limited to these examples only. Incidentally, the compound numbers described in the examples correspond to those shown in Tables 1 to 14.

EXAMPLE 1

A solution of a Grignard reagent prepared from 15.0 g of cyclopentyl bromide and 2.1 g of magnesium in tetrahydrofuran (THF) was slowly added dropwise to 100 ml of a solution of 8.7 g of N-(1-benzyl-4-piperidinyl)-phenylglyoxylic amide in THF. After the drop addition, the mixture was stirred at room temperature for 1 hour and refluxed further for 2 hours. After the reaction mixture was allowed to cool, 150 ml of water and subsequently 150 ml of 25% sulfuric acid were added dropwise to the reaction mixture. After the resultant mixture was extracted with ethyl acetate, the resulting organic layer was washed with water and dried over anhydrous sodium sulfate, and the solvent was distilled off under reduced pressure. The residue was purified by column chromatography on silica gel and subjected to recrystallization from acetone-ether, thereby obtaining 3.74 g (yield: 35.3%) of a compound of Compound No. 4 as colorless crystals.

EXAMPLE 2

Suspended in 60 ml of ethanol were 500 mg of the compound of Compound No. 4. To the suspension, 200 mg of palladium hydroxide were added to conduct hydrogenation at room temperature for 12 hours. After the catalyst was then removed by filtration, the solvent in the filtrate wad distilled off under reduced pressure to quantitatively obtain a compound of Compound No. 16.

EXAMPLE 3

Added to 380 mg of the compound of Compound No. 16 obtained in Example 2 were 7 ml of acetonitrile, 7 ml of 37% formalin and 600 mg of formic acid. The mixture was refluxed for 1 hour. After cooling the reaction mixture, aqueous sodium hydroxide was added to the reaction mixture to render it basic. After the basic reaction mixture was extracted with chloroform, the resulting organic layer was washed with water and dried over anhydrous sodium sulfate, and the solvent was then distilled off under reduced pressure. The residue was subjected to recrystallization from ether, thereby obtaining 380 mg (yield: 95.6%) of a compound of Compound No. 6 as colorless crystals.

EXAMPLE 4

Added to 380 mg of the compound of Compound No. 16 obtained in Example 2 were 7 ml of dioxane, 7 ml of water and 400 mg of potassium carbonate. While stirring the mixture, 590 mg of phenethyl bromide were added dropwise, and the resultant mixture was stirred at room temperature for 12 hours. Thereafter, 20 ml of water were added to the reaction mixture, and the resulting mixture was extracted with chloroform. The resulting organic layer was washed with water and dried over anhydrous sodium sulfate, and the solvent was then distilled off under reduced pressure. The residue was purified by column chromatography on silica gel, and the resultant crude crystals were recrystallized from ether, thereby obtaining 260 mg (yield: 46.4%) of a compound of Compound No. 8 as colorless crystals.

The date of the compounds obtained in the above examples and other compounds obtained in the same manner as an these examples are shown in the following Tables 1 to 14.

TABLE 1

| Compound No. | R¹ | R² | R³ | R⁴ | Melting Point (° C.) Fumarate | ¹H—NMR data (Fumarate DMSO-d₆, δ) |
|---|---|---|---|---|---|---|
| 1 | phenyl | cyclohexyl | H | CH₂-phenyl | 205~206.5 | 0.86–0.90(1H, m), 1.08–1.45(7H, m), 1.66–1.89(6H, m), 2.06–2.09(2H, m), 2.36–2.39(1H, m), 2.73(2H, br), 2.90(1H, s), 3.46(2H, s), 3.68–3.70(1H, m), 6.56–6.59(1H, m), 7.22–7.35(8H, m), 7.58–7.61(2H, m) |
| 2 | phenyl | cyclohexyl | H | CH₃ | 233.5~234 | 0.98–1.32(6H, m), 1.46–1.77(8H, m), 2.25–2.50(3H, m), 2.37(3H, s), 2.88–2.96(2H, m), 3.57–3.59(1H, br), 6.57(2H, s), 7.17–7.22(1H, m), 7.26–7.31(2H, m), 7.52–7.58(1H, m) |
| 3 | phenyl | cyclopropyl | H | CH₂-phenyl | 105~106.5 | 0.30–0.51(4H, m), 1.51–1.72(5H, m), 2.08–2.18(2H, m), 2.75–2.81(2H, m), 3.53(2H, s), 3.50–3.60(1H, br), 6.61(2H, s), 7.22–7.35(8H, 7.49–7.68(3H, m) |
| 4 | phenyl | cyclopentyl | H | CH₂-phenyl | 188~190 | 1.22–1.72(12H, m), 2.12–2.17(2H, m), 2.76–2.94(3H, m), 3.37–3.64(1H, br), 3.55(2H, s), 6.22(2H, s), 7.19–7.35(8H, m), 7.44–7.47(1H, m), 7.56–7.59(2H, m) |
| 5 | phenyl | cyclobutyl | H | CH₂-phenyl | 110~112 | 1.42–1.78(8H, m), 1.91–2.14(4H, m), 2.70–2.75(2H, m), 3.29–3.40(1H, m), 3.45–3.60(1H, m), 3.50(2H, s), 6.61(2H, s), 7.20–7.34(7H, m), 7.45–7.48(3H, m) |
| 6 | phenyl | cyclopentyl | H | CH₃ | 211~212 | 1.21–1.70(12H, m), 2.24–2.38(2H, m), 2.30(3H, s), 2.81–2.96(3H, m), 3.53–3.56(1H, m), 6.56(2H, s), 7.17–7.31(3H, m), 7.51(1H, d), 7.56–7.60(2H, m) |

TABLE 2

| Compound No. | R¹ | R² | R³ | R⁴ | Melting Point (° C.) Fumarate | ¹H—NMR data (Fumarate DMSO-d₆, δ) |
|---|---|---|---|---|---|---|
| 7 | phenyl | cyclopentyl | H | CH₂CH₃ | 151.5~153.5 | 1.04(3H, t), 1.20–1.27(2H, m), 1.38–1.78(10H, m), 2.22–2.32(2H, m), 2.50(2H, q), 3.57–3.59(1H, m), 6.56(2H, s), 7.18–7.21(1H, m), 7.26–7.30(2H, m), 7.52(1H, d), 7.57–7.60(2H, m) |
| 8 | phenyl | cyclopentyl | H | CH₂CH₂-phenyl | 204~205 | 1.21–1.28(2H, m), 1.34–1.70(10H, m), 2.17–2.24(2H, m), 2.58–2.64(2H, m), 2.72–2.77(2H, m), 2.87–2.97(3H, m), 3.54–3.56(1H, m), 6.60(2H, s), 7.15–7.31(8H, m), 7.47(1H, d), 7.57–7.60(2H, m) |
| 9 | phenyl | cyclopropyl | H | CH₂CH₂-phenyl | 92–94 | 0.31–0.36(1H, m), 0.42–0.51(3H, m), 1.53–1.73(5H, m), 2.10–2.28(2H, m), 2.60–2.66(2H, m), 2.72–2.78(2H, m), 2.91–2.98(2H, m), 3.60–3.62(1H, m), 6.59(2H, s), 7.15–7.34(8H, m), 7.52–7.58(3H, m) |
| 10 | phenyl | cyclopropyl | H | CH₂-(3-pyridyl) | 111~113 (2 Fumarate) | 0.31–0.35(1H, m), 0.42–0.50(3H, m), 1.52–1.70(5H, m), 2.07–2.20(2H, m), 3.55–3.57(1H, m), 6.62(2H, s), 7.49(1H, d), 7.56(2H, d), 8.45–8.49(2H, m) |
| 11 | phenyl | cyclohexyl | H | CH₂-(3-methoxyphenyl) | 209~211 | 0.97–1.72(14H, m), 2.01–2.28(3H, m), 2.71–2.77(2H, m), 3.46(2H, s), 3.43–3.54(1H, m), 3.73(3H, s), 6.61(2H, s), 6.79–6.87(3H, m), 7.17–7.30(4H, m), 7.42(1H, d), 7.55–7.59(2H, m) |

TABLE 2-continued

| Compound No. | R¹ | R² | R³ | R⁴ | Melting Point (° C.) Fumarate | ¹H—NMR data(Fumarate DMSO-d₆, δ) |
|---|---|---|---|---|---|---|
| 12 | 4-Cl-C₆H₄- | cyclopentyl | H | CH₂-C₆H₅ | 203~204 | 1.18–1.68(12H, m), 2.02–2.10(2H, m), 2.72–2.91 (3H, m), 3.48(2H, s), 3.48–3.52(1H, m), 6.61(2H, s), 7.22–7.35(7H, m), 7.46(1H, d), 7.60(2H, m) |

TABLE 3

| Compound No. | R¹ | R² | R³ | R⁴ | Melting Point (° C.) Fumarate | ¹H—NMR data(Fumarate DMSO-d₆, δ) |
|---|---|---|---|---|---|---|
| 13 | 4-CF₃-C₆H₄- | cyclopentyl | H | CH₂-C₆H₅ | 133~135 | 1.20–1.70(12H, m), 2.03–2.11(2H, m), 2.70–2.96(3H, m), 3.49(2H, s), 3.49–3.53(1H, m), 6.61(2H, s), 7.24–7.33(5H, m), 7.53(1H, d), 7.65(2H, d), 7.81(2H, d) |
| 14 | 4-CH₃-C₆H₄- | cyclopentyl | H | CH₂-C₆H₅ | 147~149 | 1.22–1.65(12H, m), 2.05–2.11(2H, m), 2.25(3H, s), 2.69–2.93(3H, m), 3.51 (2H, s), 3.48–3.51(1H, m), 6.61(2H, s), 7.07(2H, d), 7.24–7.45(8H, m) |
| 15 | 4-OCH₃-C₆H₄- | cyclopentyl | H | CH₂-C₆H₅ | 118~120 | 1.23–1.65(12H, m), 2.03–2.08(2H, m), 2.69–2.92(3H, m), 3.41–3.51(1H, m), 3.47(2H, s), 3.72(3H, s), 6.61(2H, s), 6.83(2H, d), 7.24–7.48(8H, m) |
| 16 | C₆H₅- | cyclopentyl | H | H | 215~216 | 1.22–1.81(12H, m), 2.73–2.96(3H, m), 3.67–3.73(1H, m), 6.45(2H, s), 7.17–7.23(1H, m), 7.26–7.31(2H, m), 7.56–7.60(2H, m), 7.65(1H, d) |
| 17 | 2-thienyl | cyclopentyl | H | CH₂-C₆H₅ | 95~100 | 1.36–1.70(12H, m), 2.06–2.13(2H, m), 2.73–2.75(3H, m), 3.51(2H, s), 3.51–3.57(1H, m), 6.61(2H, s), 6.92(1H, dd), 7.07(1H, dd), 7.23–7.34(6H, m), 7.49(1H, d) |

TABLE 4

| Compound No. | R¹ | R² | R³ | R⁴ | Melting Point (° C.) Fumarate | ¹H—NMR data(Fumarate DMSO-d₆, δ) |
|---|---|---|---|---|---|---|
| 18 | phenyl | cyclopropyl | H | CH₂-C₆H₄-OMe (para) | 92~94 | 0.30–0.50(4H, m), 1.50–1.72(5H, m), 2.08–2.15(2H, m), 2.74–2.80(2H, m), 3.47(2H, s), 3.55–3.60(1H, m), 3.74(3H, s), 6.61(2H, s), 6.86–6.90(2H, m), 7.19–7.33 (5H, m), 7.53–7.57(2H, m) |
| 19 | phenyl | cyclopentyl | H | CH₂-C₆H₄-F (meta) | 194~196 | 1.20–1.69(12H, m), 2.00–2.09(2H, m), 2.66–2.74(2H, m), 2.91–2.96(1H, m), 3.46–3.57(1H, m), 3.48(2H, s), 5.46(1H, br), 6.62(2H, s), 7.02–7.38(7H, m), 7.42(1H, d), 7.58(2H, d) |
| 20 | phenyl | cyclopentyl | H | CH₂-C₆H₄-CN | 190~192 (Hydrochloride) | (Free): 1.21–1.69(12H, m), 1.99–2.08(2H, m), 2.63–2.71(2H, m), 2.91–2.96(1H, m), 3.45–3.55(1H, m), 3.50(2H, s), 5.46(1H, s), 7.17–7.71(9H, m), 7.42(1H, d) |
| 21 | phenyl | cyclopentyl | H | CH₂-C₆H₄-OCH₃ (meta) | 196~197.5 | 1.22–1.69(12H, m), 2.02–2.11(2H, m), 2.69–2.77(2H, m), 2.91–2.96(1H, m), 3.45–3.53(1H, m), 3.46(2H, s), 6.61(2H, s), 6.79–6.87(3H, m), 7.17–7.30 (4H, m), 7.44(2H, d), 7.56–7.59(2H, m) |
| 22 | phenyl | cyclohexyl | H | CH₂-C₆H₄-OH | 172~175 | 0.97–1.72(14H, m), 2.02–2.12(2H, m), 2.21–2.25(1H, m), 2.68–2.77(2H, m), 3.73(2H, s), 3.50–3.58(1H, m), 6.61(2H, s), 6.64–6.87(3H, m), 7.06–7.30(4H, m), 7.42(1H, d), 7.55–7.58(2H, m) |

TABLE 5

| Compound No. | R¹ | R² | R³ | R⁴ | Melting Point (° C.) Fumarate | ¹H—NMR data(Fumarate DMSO-d₆, δ) |
|---|---|---|---|---|---|---|
| 23 | phenyl | isopropyl | H | CH₂-phenyl | 183~185 | 0.59(3H, d), 0.88(3H, d), 1.43–1.55(3H, m), 1.68–1.71(1H, m), 2.03–2.11(2H, m), 2.63–2.76(3H, m), 3.48(2H, s), 3.48–3.52(1H, m), 6.61(2H, s), 7.18–7.44(9H, m), 7.58(2H, d) |
| 24 | phenyl | cyclopentyl | H | CH=CH-CH₂-phenyl (styryl propenyl) | 177~178 | 1.22–1.70(12H, m), 2.08–2.18(2H, m), 2.80–2.18(2H, m), 2.80–2.97(3H, m), 3.15(2H, d), 3.48–3.58(1H, m), 6.23–6.32(1H, m), 6.53(1H, d), 6.58(2H, s) 7.17–7.60(10H, m), 7.46(1H, d) |
| 25 | phenyl | cyclopentyl | H | C₆H₄-CH₃ | 185.5~187 | 1.21–1.78(12H, m), 2.68–2.80(2H, m), 2.92–2.98(1H, m), 3.56–3.69(3H, m), 5.45(1H, br), 6.63(2H, s), 6.73(1H, t), 6.90(2H, d), 7.15–7.31(5H, m), 7.51(1H, d), 7.59(2H, d) |
| 26 | phenyl | sec-butyl (CH(CH₃)CH₂CH₃) | H | CH₂-phenyl | 190~193 | 0.66(3H, t), 0.90(3H, t), 1.02–1.10(2H, m), 1.28–1.55(5H, m), 1.68–1.71(1H, m), 2.07–2.16(3H, m), 2.70–2.78(2H, m), 3.51(3H, s and m), 6.61(2H, s), 7.17–7.33(8H, m), 7.44(1H, d), 7.59(2H, d) |

TABLE 5-continued

| Compound No. | R¹ | R² | R³ | R⁴ | Melting Point (° C.) Fumarate | ¹H—NMR data(Fumarate DMSO-d₆, δ) |
|---|---|---|---|---|---|---|
| 27 | 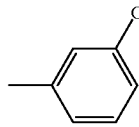 | Et | H | 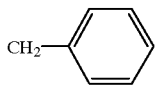 | 90~93 | 0.78(3H, t), 1.46–1.58(3H, m), 1.69–1.85(2H, m), 2.08–2.18(3H, m), 2.73–2.80(2H, m), 3.53(2H, s), 3.53–3.57(1H, m), 3.73(3H, s), 6.61(2H, s), 6.79(1H, m), 7.09–7.18(2H, m), 7.20–7.34(6H, m), 7.50(2H, d) |

TABLE 6

| Compound No. | R¹ | R² | R³ | R⁴ | Melting Point (° C.) Fumarate | ¹H—NMR data(Fumarate DMSO-d₆, δ) |
|---|---|---|---|---|---|---|
| 28 | 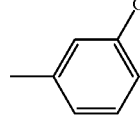 |  | H | 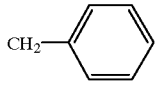 | 96~99 | 0.6(3H, d), 0.87(3H, d), 1.44–1.56(3H, m), 1.68–1.71(1H, m), 2.05–2.14(2H, m), 2.60–2.77(3H, m), 3.51(2H, s), 3.51–3.54(1H, m), 3.73(3H, s), 6.61(2H, s), 6.79(1H, m), 7.15–7.33(8H, m), 7.43(1H, d) |
| 29 | 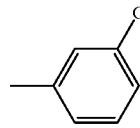 | 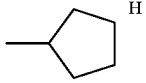 | H | 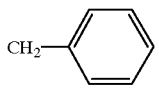 | 95~98 | 1.21–1.66(12H, m), 2.08–2.11(2H, m), 2.72–2.93(3H, m), 3.51(2H, s), 3.51–3.54(1H, m), 3.73(3H, s), 6.61(2H, s), 6.76–6.79(1H, m), 7.14–7.34(8H, m), 7.44(1H, d) |
| 30 | 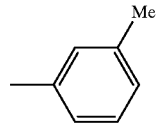 | Et | H | 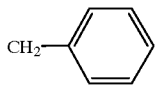 | 88~91 | 0.78(3H, t), 1.45–1.58(3H, m), 1.69–1.85(2H, m), 2.06–2.17(3H, m), 2.28(3H, s), 2.72–2.79(2H, m), 3.51(2H, s), 3.51–3.56(1H, m), 6.61(2H, s), 7.01–7.03(1H, m), 7.15–7.35(8H, m), 7.46(1H, d) |
| 31 | 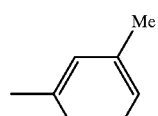 |  | H | 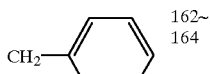 | 162~164 | 0.59(3H, d), 0.87(3H, d), 1.44–1.71(4H, m), 2.07–2.15(2H, m), 2.29(3H, s), 2.62–2.78(3H, m), 3.52(2H, s), 3.52–3.53(1H, m), 6.61(2H, s), 7.00–7.02(1H, m), 7.15–7.43(9H, m) |
| 32 | 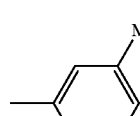 | 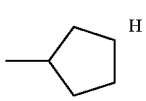 | H | 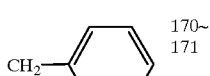 | 170~171 | (CDCl₃); 1.21–1.69(12H, m), 2.05–2.14(2H, m), 2.28(3H, s), 2.71–2.77(2H, m), 2.90–2.94(1H, m), 3.50(2H, s), 3.50–3.52(1H, m), 6.61(2H, s), 7.00–7.02(1H, m), 7.16–7.43(9H, m) |

TABLE 7

| Compound No. | R¹ | R² | R³ | R⁴ | Melting Point (° C.) Fumarate | ¹H—NMR data(Fumarate DMSO-d₆, δ) |
|---|---|---|---|---|---|---|
| 33 | 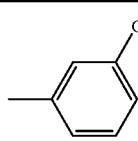 | Et | H | 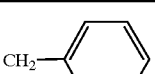 | 90~93 | 0.78(3H, t), 1.47–1.86(5H, m), 2.07–2.16(3H, m), 2.73–2.81(2H, m), 3.53(2H, s), 3.53–3.58(1H, m), 6.61(2H, s), 7.24–7.57(10H, m) |

TABLE 7-continued

| Compound No. | R¹ | R² | R³ | R⁴ | Melting Point (° C.) Fumarate | ¹H—NMR data(Fumarate DMSO-d₆, δ) |
|---|---|---|---|---|---|---|
| 34 | 3-Cl-phenyl | isopropyl | H | CH₂-phenyl | 175~177 | 0.59(3H, d), 0.88(3H, d), 1.45–1.71(4H, m), 2.04–2.14 (2H, m), 2.61–2.78(3H, m), 3.51(2H, s), 3.51–3.54(1H, m), 6.61(2H, s), 7.22–7.35(7H, m), 7.50–7.62(3H, m) |
| 35 | 3-Cl-phenyl | cyclopentyl | H | CH₂-phenyl | 176~178 | 1.21–1.69(12H, m), 2.04–2.12(2H, m), 2.71–2.91(3H, m), 3.50(2H, s), 3.50–3.54(1H, m), 6.61(2H, s), 7.23–7.34(7H, m), 7.49–7.62(3H, m) |
| 36 | 3-CF₃-phenyl | Et | H | CH₂-phenyl | 84~87 | 0.79(3H, t), 1.47–1.89(5H, m), 2.05–2.20(3H, m), 2.72–2.80(2H, m), 3.52(2H, s), 3.52–3.57(1H, m), 6.61(2H, s), 7.23–7.34(5H, m), 7.52–7.64(3H, m), 7.84–7.88(2H, m) |
| 37 | 3-CF₃-phenyl | isopropyl | H | CH₂-phenyl | 95~98 | 0.58(3H, d), 0.90(3H, d), 1.48–1.69(4H, m), 2.04–2.13 (2H, m), 2.62–2.78(3H, m), 3.50(2H, s), 3.50–3.55(1H, m), 6.61(2H, s), 7.23–7.34(5H, m), 3.52–7.60(3H, m), 7.89–7.93(2H, m) |

TABLE 8

| Compound No. | R¹ | R² | R³ | R⁴ | Melting Point (° C.) Fumarate | ¹H—NMR data(Fumarate DMSO-d₆, δ) |
|---|---|---|---|---|---|---|
| 38 | 3-CF₃-phenyl | cyclopentyl | H | CH₂-phenyl | 102~104 | 1.21–1.70(12H, m), 2.03–2.13(2H, m), 2.71–2.95(3H, m), 3.50(2H, s), 3.50–3.54(1H, m), 6.61(2H, s), 7.23–7.33 (5H, m), 7.52–7.58(3H, m), 7.89–7.92(2H, m) |
| 39 | phenyl | isopropyl | H | CH₂-(3-CN-phenyl) | 95~97 (Hydrochloride) | (Free): 0.59(3H, d), 0.88(3H, d), 1.41–1.55(4H, m), 1.66–1.70(1H, m), 1.90–2.08(2H, m), 2.61–2.71(3H, m), 3.45–3.53(1H, m), 3.49(2H, s), 7.18–7.31(3H, m), 7.41(1H, d, J—8.3Hz), 7.50–7.71(6H, m) |
| 40 | phenyl | isopropyl | H | CH₂-(4-CN-phenyl) | 139~141 | 0.60(3H, d), 0.88(3H, d), 1.42–1.55(4H, m), 1.67–1.71(1H, m), 2.01–2.12(2H, m), 2.59–2.72(3H, m), 3.50–3.57 (1H, m), 3.54(2H, s), 6.62(2H, s), 7.18–7.31(3H, m), 7.42(1H, d), 7.49(2H, d), 7.58(2H, d) |
| 41 | phenyl | isopropyl | H | CH₂-(3-COOMe-phenyl) | 165~167 | 0.60(3H, d), 0.88(3H, d), 1.43–1.71(4H, m), 2.04–2.15 (2H, m), 2.61–2.76(3H, m), 3.50–3.56(1H, m), 3.55(2H, s), 3.85(3H, s), 6.62(2H, s), 7.18–7.31(3H, m), 7.43–7.60(5H, m), 7.84(1H, d), 7.90(1H, s) |
| 42 | phenyl | isopropyl | H | CH₂-(4-COOMe-phenyl) | 182~184 | 0.60(3H, d), 0.88(3H, d), 1.45–1.68(4H, m), 2.03–2.08 (2H, m), 2.61–2.73(3H, m), 3.49–3.54(1H, m), 3.53(2H, s), 3.84(3H, s) 6.62(2H, s), 7.18–7.31(3H, m), 7.43(3H, d), 7.57–7.60(2H, m), 7.90(2H, d) |

TABLE 9

| Compound No. | R¹ | R² | R³ | R⁴ | Melting Point (° C.) Fumarate | ¹H—NMR data(Fumarate DMSO-d₆, δ) |
|---|---|---|---|---|---|---|
| 43 | phenyl (4-methyl) | isopropyl | H | CH₂-C₆H₄-F (4-F) | 141~143 | 0.59(3H, d), 0.87(3H, d), 1.41–1.71(4H, m), 2.00–2.07(2H, m), 2.61–2.74(3H, m), 3.45(2H, s), 3.44–3.53(1H, m), 6.61(2H, s), 7.09–7.33(7H, m), 7.42(1H, m), 7.57–7.60(2H, m) |
| 44 | phenyl (4-methyl) | isopropyl | H | CH₂CH₂-phenyl | 199~200 | 0.60(3H, d), 0.89(3H, d), 1.50–1.77(4H, m), 2.27–2.38(2H, m), 2.60–2.80(5H, m), 2.95–3.03(2H, m), 3.56–3.61(1H, m), 6.59(2H, s), 7.16–7.32(8H, m), 7.51(1H, m), 7.58–7.61(2H m) |
| 45 | 2-thienyl | isopropyl | H | CH₂-phenyl | 95~99 | 0.72(3H, d), 0.84(3H, d), 1.49–1.71(4H, m), 2.06–2.13(2H, m), 2.41–2.49(1H, m), 2.72–2.77(2H, m), 3.50(2H, s), 3.54–3.58(1H, m), 6.61(2H, s), 6.93(1H, dd), 7.06(1H, dd), 7.23–7.34(6H, m), 7.48(1H, d) |
| 46 | phenyl (4-methyl) | isopropyl | H | CH₂CH₂-C₆H₄-NO₂ (3-NO₂) | 169~172 | 0.60(3H, d), 0.88(3H, d), 1.44–1.57(3H, m), 1.68–1.72(1H, m), 2.04–2.15(2H, m), 2.59–2.76(3H, m), 3.50–3.58(1H, m), 3.60(2H, s), 6.62(2H, s), 7.18–7.20(1H, m), 7.21–7.31(2H, m), 7.44(1H, d), 7.57–7.64(3H, m) |
| 47 | phenyl (4-methyl) | isopropyl | H | CH₂CH₂-C₆H₄-NH₂ (3-NH₂) | 197~199 | 0.60(3H, d), 0.88(3H, d), 1.41–1.57(3H, m), 1.67–1.73(1H, m), 2.00–2.15(2H, m), 2.59–2.78(3H, m), 3.34(2H, s), 3.46–3.55(1H, m), 6.40–6.46(2H, m), 6.51(1H, s), 6.60(2H, s), 6.90–6.96(1H, m), 7.18–7.32(3H, m), 7.43(1H, d), 7.57–7.60(2H, m) |

TABLE 10

| Compound No. | R¹ | R² | R³ | R⁴ | Melting Point (° C.) Fumarate | ¹H—NMR data(Fumarate DMSO-d₆, δ) |
|---|---|---|---|---|---|---|
| 48 | 2-pyridyl (6-methyl) | isopropyl | H | CH₂-phenyl | 100~103 | 0.45(3H, d), 0.89(3H, d), 1.45–1.70(4H, m), 2.03–2.13(2H, m), 2.60–2.73(3H, m), 3.48(2H, s), 3.48–3.57(1H, m), 5.90(1H, br), 6.61(2H, s), 7.22–7.38(6H, m), 7.78–7.87(3H, m), 8.52–8.53(1H, m) |
| 49 | 2-pyridyl (6-methyl) | cyclopentyl | H | CH₂-phenyl | 110~112 | 1.00–1.11(2H, m), 1.37–1.69(10H, m), 2.06–2.13(2H, m), 2.67–2.74(2H, m), 2.88–2.94(1H, m), 3.50(2H, s), 3.50–3.57(1H, m), 6.00(1H, br), 6.61(2H, s), 7.23–7.37(6H, m), 7.76–7.86(3H, m), 8.51–8.52(1H, m) |
| 50 | 2,4-difluorophenyl | isopropyl | H | CH₂-phenyl | 162~166 | 0.80(3H, d), 0.86(3H, dd), 1.48–1.68(4H, m), 2.08–2.14(2H, m), 2.74–2.86(3H, m), 3.50(2H, s), 3.50–3.56(1H, m), 6.61(2H, s), 6.65–6.73(1H, m), 7.02–7.10(1H, m), 7.23–7.48(6H, m), 7.58–7.62(1H, m) |
| 51 | 3-pyridyl | isopropyl | H | CH₂-phenyl | 105~110 | 0.62(3H, d), 0.89(3H, d), 1.48–1.71(4H, m), 2.03–2.13(2H, m), 2.61–2.77(3H, m), 3.49(2H, s), 3.49–3.54(1H, m), 6.61(2H, s), 7.22–7.33(6H, m), 7.55(1H, d), 7.93(1H, ddd), 8.42(1H, dd), 8.77(1H, d) |
| 52 | 3-pyridyl | cyclopentyl | H | CH₂-phenyl | 164~166 | 1.22–1.70(12H, m), 2.03–2.13(2H, m), 2.71–2.78(2H, m), 2.91–2.95(1H, m), 3.50(2H, s), 3.50–3.55(1H, m), 6.61(2H, s), 7.23–7.33(6H, m), 7.55(1H, d), 7.93(1H, ddd), 8.40(1H, dd), 8.77(1H, d) |

TABLE 11

| Compound No. | R¹ | R² | R³ | R⁴ | Melting Point (° C.) rate | ¹H—NMR data(Fumarate DMSO-d₆, δ) |
|---|---|---|---|---|---|---|
| 53 | phenyl | cyclopentyl | H | 3-aminophenyl-ethyl | 107~110 (2 Fumarate) | 1.18–1.75(12H, m), 2.24–2.39(2H, m), 2.80–3.02(3H, m), 3.52(2H, s), 3.50–3.65(1H, m), 6.48(2H, t), 7.17–7.31 (3H, m), 7.51(1H, d), 7.58(2H, d) |
| 54 | 4-OMe-phenyl | isopropyl | H | CH₂-phenyl | 145~148 | 0.60(3H, d), 0.86(3H, d), 1.43–1.71(4H, m), 2.06–2.16 (2H, m), 2.57–2.71(1H, m), 2.74–2.78(2H, m), 3.52 (2H, s), 3.52–3.54(1H, m), 3.72(3H, s), 6.61(2H, s), 6.83(2H, d), 7.23–7.39(5H, m), 7.40(1H, d), 7.49(2H, d) |
| 55 | 4-CF₃-phenyl | isopropyl | H | CH₂-phenyl | 160–166 | 0.59(3H, d), 0.90(3H, d), 1.44–1.72(4H, m), 2.03–2.14 (2H, m), 2.63–2.78(3H, m), 3.50(2H, s), 3.50–3.57 (1H, m), 6.62(2H, s), 7.23–7.33(5H, m), 7.53(1H, d), 7.66(2H, d), 7.81(2H, d) |
| 56 | 4-Me-phenyl | isopropyl | H | CH₂-phenyl | 112~117 | 0.59(3H, d), 0.86(3H, d), 1.42–1.71(4H, m), 2.06–2.15 (2H, m), 2.26(3H, s), 2.50–2.64(1H, m), 2.70–2.77 (2H, m), 3.44–3.54(1H, m), 3.51(2H, s), 6.61(2H, s), 7.08(2H, d), 7.22–7.34(5H, m), 7.40(2H, d), 7.45(2H, d) |
| 57 | 2-Me-phenyl | isopropyl | H | CH₂-phenyl | 107~110 | 0.74(3H, d), 0.90(3H, d), 1.38–1.51(4H, m), 1.93–2.02 (2H, m), 2.28(3H, s), 2.69–2.74(2H, m), 2.89–2.96 (1H, m), 3.37–3.45(1H, m), 3.45(2H, s), 6.61(2H, s), 7.06–7.43(9H, m), 7.45(1H, d) |

TABLE 12
| Compound No. | R¹ | R² | R³ | R⁴ | Melting Point (° C.) Fumarate | ¹H—NMR data(Fumarate DMSO-d₆, δ) |
|---|---|---|---|---|---|---|
| 58 |  |  | H |  | 218–220 (½ Fumarate) | 0.59(3H, d), 0.87(3H, d), 1.45–1.67(4H, m), 2.03–2.08 (2H, m), 2.60–2.62(1H, m), 2.69–2.76(2H, m), 3.33 (2H, s), 3.50–3.52(1H, m), 3.73(3H, s), 6.41–6.45 (2H, m), 6.51(1H, s), 6.61(1H, m), 6.76–6.79(1H, m), 6.91–6.95(1H, m), 7.15–7.22(3H, m), 7.42(1H, d) |
| 59 |  |  | H |  | 160–165 (decomp.) (2 Hydrochloride) | 0.59(3H, d), 0.88(3H, d), 1.75–2.09(4H, m), 2.93–3.92 (6H, m), 4.21(2H, s), 7.24(2H, d), 7.43(3H, m), 7.73(1H, d), 7.62–7.75(4H, m) |
| 60 |  |  | H |  | 183–184 | 0.82–1.17(5H, m), 1.40–1.78(1H, m), 2.03–2.15(3H, m), 2.69–2.78(2H, m), 3.48–3.55(1H, m), 3.49(1H, s), 6.61(2H, s), 7.17–7.34(8H, m), 7.48(1H, d), 7.52–7.55 (2H, m) |
| 61 |  |  | H |  | 187 | 1.19–1.51(4H, m), 1.99–2.09(2H, m), 2.59–2.67(2H, m), 3.05(1H, d), 3.37–3.50(1H, m), 3.45(2H, s), 3.55(1H, d), 7.11–7.33(14H, m), 7.58–7.61(2H, m) |
| 62 |  |  | H | (2-nitrobenzyl) | 189–192 | 0.59(3H, d), 0.87(3H, d), 1.32–1.51(3H, m), 1.63–1.67 (1H, m), 2.01–2.10(2H, m), 2.50–2.67(3H, m), 3.46–3.55 (1H, m), 3.69(2H, s), 5.40(1H, br), 6.63(2H, s), 7.15–7.67(8H, m), 7.40(1H, d), 7.81–7.84(1H, m) |

TABLE 13

| Compound No. | R¹ | R² | R³ | R⁴ | Melting Point (° C.) Fumarate | ¹H—NMR data(Fumarate DMSO-d₆, δ) |
|---|---|---|---|---|---|---|
| 63 | phenyl | isopropyl | H | benzyl with 2-NH₂ | 178–179 | 0.60(3H, d), 0.88(3H, d), 1.38–1.56(3H, m), 1.67–1.72 (1H, m), 1.97–2.06(2H, m), 2.61–2.73(3H, m), 3.38 (2H, s), 3.49–3.53(1H, m), 6.46–6.50(1H, m) 6.60–6.62 (1H, m), 6.61(2H, s), 6.89–6.99(2H, m), 7.18–7.31(3H, m), 7.42(1H, d), 7.57–7.60(2H, m) |
| 64 | phenyl | isopropyl | H | benzyl with 4-NO₂ | 154–156 (½ Fumarate) | 0.60(3H, d), 0.88(3H, d), 1.43–1.56(3H, m), 1.67–1.72 (1H, m), 2.02–2.12(2H, m), 2.59–2.73(3H, m), 3.44–3.55 (1H, m), 3.58(2H, s), 5.42(1H, br), 6.62(1H, s), 7.18–7.31(3H, m), 7.42(1H, d), 7.55–7.60(4H, m) |
| 65 | phenyl | isopropyl | H | benzyl with 4-NH₂ | 169–171 | 0.59(3H, d), 0.88(3H, d), 1.42–1.54(3H, m), 1.67–1.71 (1H, m), 2.03–2.14(2H, m), 2.60–2.79(3H, m), 3.37 (2H, s), 3.50–3.53(1H, m), 6.48–6.51(2H, m), 6.57 (2H, s), 6.91–6.93(2H, m), 7.18–7.30(3H, m), 7.44(1H, d), 7.57–7.59(2H, m) |
| 66 | 4-OMe-phenyl | cyclopentyl | H | phenyl with 3-NH₂ | 124–127 | 1.26–1.73(12H, m), 2.00–2.08(2H, m), 2.69–2.76 (2H, m), 2.86–2.92(1H, m), 3.32(2H, s), 3.49(1H, m), 3.72(3H, s), 6.41–6.51(3H, m), 6.56(2H, s), 6.83 (2H, d), 6.91–6.94(1H, m), 7.39(1H, d), 7.47(2H, d) |
| 67 | 3-pyridyl | isopropyl | H | phenyl with 3-NH₂ | 100–105 | 0.62(3H, d), 0.90(3H, d), 1.48–1.58(3H, m), 1.70(1H, m), 2.05–2.18(2H, m), 2.60–2.67(1H, m), 2.75–2.82(2H, m), 3.40(2H, s), 3.48–3.56(1H, m), 6.43–6.59(2H, m), 6.61(2H, s), 6.94(1H, dd), 7.33(1H, d), 7.58(1H, d), 7.93(1H, m), 8.42(1H, dd), 8.77(1H, d) |

TABLE 14

| Compound No. | R¹ | R² | R³ | R⁴ | Melting Point (° C.) Fumarate | ¹H—NMR data(Fumarate DMSO-d$_6$, δ) |
|---|---|---|---|---|---|---|
| 68 | -C₆H₅ | -CH(CH₃)- | H | -CH₂CH₂-C₆H₄-NH₂ | 187~190 | 0.60(3H, d), 0.89(3H, d), 1.49–1.76(4H, m), 2.20–2.38 (2H, m), 2.57–2.72(5H, m), 2.88–2.97(2H, m), 3.52–3.64 (1H, m), 6.58(2H, s), 6.46–7.60(1H, m) |
| 69 | -C₆H₅ | -CH(CH₃)- | Me | -CH₂-C₆H₅ | oil | (CDCl₃); 0.90–1.30(6H, m), 1.30–2.30(4H, m), 2.50–3.10(5H, m), 2.60(1.5H, s), 2.90(1.5H, s), 3.30–3.60(1H, m), 3.40(1H, s), 3.50(1H, s), 7.10–7.50 (10H, m) |
| 70 | -C₆H₅ | -CH=CH- | H | -CH₂-C₆H₅ | 125~127 | 1.53–1.69(4H, m), 2.14–2.19(2H, m), 2.79–2.83(2H, m), 3.57–3.60(1H, m), 3.58(2H, s), 5.21(1H, d), 5.38(1H, d), 6.46(1H, dd), 6.61(2H, s), 7.72–7.45 (10H, m), 7.63(1H, d) |

Referential Example 1

Added to 4.28 g of ethyl phenylglyoxylate were 9.12 g of 4-amino-1-benzylpiperidine. The mixture was heated and stirred at 120° C. for 3 hours on an oil bath. Thereafter, ethanol formed was distilled off under reduced pressure, and the residue was purified by column chromatography on silica gel, thereby obtaining 6.3 g (yield: 81.4%) of N-(1-benzyl-4-piperidinyl)phenyl-glyoxylic acid amide.

¹H-NMR (CDCl₃, δ): 1.25–2.38(6H,m), 2.63–3.02(2H, m), 3.52(2H,s), 3.86(1H,br), 6.98(1H,br), 7.22–7.83(8H,m), 8.23–8.50(2H,m).

Test Example 1

Anticholinergic Effect on Bladder Specimens Enucleated From Rats

1) Testing Method

Male S.D. rats weighing 220–450 g were exsanguinated to death to enucleate their bladders, thereby preparing vertically split specimens (3–5 mm wide by 10–15 mm long) with each triangular part removed therefrom. Each of the specimens was suspended in a Magnus bath filled with a Tyrode's solution (32° C.) aerated by a mixed gas (95% O₂, 5% CO₂) with a load of 0.5 g applied thereto. The response of the specimen was recorded in terms of isometric contraction through a tension transducer. After the stability of the specimen was attained, an effect on contraction caused by acetylcholine ($10^{-5}$ M) was investigated. Incidentally, agents to be tested were applied to the individual specimens in advance for 5 minutes before the test to investigate their effects.

The results are shown in Table 15.

TABLE 15

| Compound No. | IC$_{50}$ (M) | Compound No. | IC$_{50}$ (M) |
|---|---|---|---|
| 1 | 3.20 × 10⁻⁸ | 29 | 8.50 × 10⁻⁷ |
| 2 | 4.34 × 10⁻⁷ | 34 | 2.80 × 10⁻⁷ |
| 3 | 2.70 × 10⁻⁸ | 35 | 2.00 × 10⁻⁷ |
| 4 | 3.36 × 10⁻⁸ | 49 | 6.50 × 10⁻⁹ |
| 15 | 1.30 × 10⁻⁷ | 56 | 1.68 × 10⁻⁷ |
| 23 | 6.60 × 10⁻⁸ | Propiverine hydrochloride | 7.84 × 10⁻⁷ |

Test Example 2

Calcium Antagonism Against Bladder Specimens Enucleated From Rats

1) Testing Method

After removal of calcium ion in specimens prepared in accordance with the testing method of Test Example 1 by adding 1 mM EDTA, $10^{-3}$ M calcium chloride was applied to the specimens. After contraction caused by calcium chloride was stable, each of agents to be tested was applied cumulatively to the specimen. Assuming that the contraction upon the first application of the test agent was 100%, a value obtained by subtracting a spontaneous relaxation rate of a specimen, to which no agent was applied, from an inhibiting rate upon the application of the agent of varied concentrations was regarded as a contraction inhibiting rate.

The results are shown in Table 16.

TABLE 16

| Compound No. | IC$_{30}$ (M) |
|---|---|
| 1 | 2.66 × 10⁻⁶ |
| 3 | 2.66 × 10⁻⁵ |
| 4 | 2.85 × 10⁻⁶ |
| Propiverine hydrochloride | 1.21 × 10⁻⁵ |

What is claimed is:

1. A substituted piperdine derivative having the formula (1):

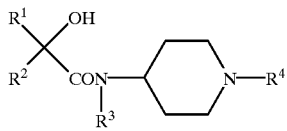

(I)

wherein
R$^1$ is an unsubstituted phenyl group, a phenyl group substituted with 1 to 3 radicals, a naphthyl group, or a naphthyl group substituted with 1 to 3 radicals, wherein said radicals are selected from the group consisting of a halogen atom, an unsubstituted C$_{1-6}$ alkyl group, a halogenated C$_{1-6}$ alkyl group, a C$_{1-6}$ alkoxyl group, an amino group, a benzyloxy group, a cyano group, a benzoyl group, a C$_{1-6}$ alkanoyl group, a carbamoyl group, carboxyl group, a C$_{1-6}$ alkanoyloxy group, a nitro group and a sulfonamide group;

R$^2$ is a linear alkyl group having 1 to 8 carbon atoms, a branched alkyl group having 1 to 8 carbon atoms, a cyclic alkyl group having 3 to 8 carbon atoms, a cyclic-linear alkyl group having 4 to 8 carbon atoms, an alkenyl group having 2 to 6 carbon atoms, or a C$_{1-6}$ alkyl group substituted with a phenyl group;

R$^3$ is a hydrogen atom or an alkyl group having 1 to 6 carbon atoms; and

R$^4$ is an unsubstituted phenyl group, a phenyl group substituted with 1 to 3 substituents, an unsubstituted naphthyl group, a naphthyl group substituted with 1 to 3 substituents, an unsubstituted phenyl-C$_{1-6}$-alkyl group, a phenyl-C$_{1-6}$-alkyl group substituted with 1 to 3 substituents, an unsubstituted phenyl-C$_{2-6}$-alkenyl group, or a phenyl-C$_{2-6}$-alkenyl group substituted with 1 to 3 substituents, wherein said substituents are selected from the group consisting of a C$_{1-6}$ alkoxyl group, a halogen atom, a cyano group, a hydroxyl group, a nitro group, an amino group, a C$_{1-6}$ alkylamino group and a C$_{1-6}$ alkoxycarbonyl group;

or a salt thereof.

2. The substituted piperidine of claim 1, wherein

R$^1$ is an unsubstituted phenyl group, or a phenyl group substituted with 1 to 3 radicals, wherein said radicals are selected from the group consisting of a halogen atom, an unsubstituted C$_{1-6}$ alkyl group, a halogenated C$_{1-6}$ alkyl group, a C$_{1-6}$ alkoxyl group, and an amino group;

R$^2$ is a linear alkyl group having 1 to 8 carbon atoms, a branched alkyl group having 1 to 8 carbon atoms, a cyclic alkyl group having 3 to 8 carbon atoms, a cyclic-linear alkyl group having 4 to 8 carbon atoms, an alkenyl group having 2 to 6 carbon atoms, or a phenyl-C$_{1-6}$-alkyl group;

R$^3$ is a hydrogen atom or an alkyl group having 1–6 carbon atoms; and

R$^4$ is a phenyl group, an unsubstituted phenyl-C$_{1-6}$-alkyl group, a phenyl-C$_{1-6}$-alkyl group substituted with 1 to 3 substituents, an unsubstituted phenyl-C$_{2-6}$-alkenyl group, or a phenyl-C$_{2-6}$-alkenyl group substituted with 1 to 3 substituents, wherein said substituents are selected from the group consisting of a C$_{1-6}$ alkoxyl group, a halogen atom, a cyano group, a hydroxyl group, a nitro group, an amino group, a C$_{1-6}$ alkylamino group, and a C$_{1-6}$ alkoxycarbonyl group.

3. The substituted piperidine derivative of claim 1, wherein R$^1$ is an unsubstituted phenyl group.

4. The substituted piperdine of claim 1, wherein R$^1$ is said substituted phenyl group.

5. A pharmaceutical composition, comprising an effective amount of the substituted piperidine of claim 1 and a pharmaceutically acceptable carrier.

6. A method of treating a urinary disturbance, comprising administering an effective amount of the substituted piperidine of claim 1 to a patient in need thereof.

* * * * *